United States Patent
Atkinson, Jr.

(10) Patent No.: US 9,919,022 B2
(45) Date of Patent: Mar. 20, 2018

(54) USE OF ANGIOTENSIN II (AII) RECEPTOR AGONISTS TO PREVENT OR REDUCE HEMODIALYSIS-ASSOCIATED SKELETAL MUSCLE CRAMPS

(71) Applicant: Arthur J. Atkinson, Jr., Richland, MI (US)

(72) Inventor: Arthur J. Atkinson, Jr., Richland, MI (US)

( * ) Notice: Subject to any disclaimer, the term of this patent is extended or adjusted under 35 U.S.C. 154(b) by 0 days.

(21) Appl. No.: 14/933,862

(22) Filed: Nov. 5, 2015

(65) Prior Publication Data

US 2016/0271205 A1 Sep. 22, 2016

Related U.S. Application Data

(60) Provisional application No. 62/135,981, filed on Mar. 20, 2015.

(51) Int. Cl.
| | |
|---|---|
| *A61K 38/08* | (2006.01) |
| *A61P 21/00* | (2006.01) |
| *A61K 38/48* | (2006.01) |
| *C07K 7/14* | (2006.01) |

(52) U.S. Cl.
CPC .......... *A61K 38/085* (2013.01); *A61K 38/488* (2013.01); *A61K 38/4813* (2013.01); *C12Y 304/15001* (2013.01); *C12Y 304/23015* (2013.01)

(58) Field of Classification Search
None
See application file for complete search history.

(56) References Cited

U.S. PATENT DOCUMENTS

2011/0144026 A1 6/2011 Chawla
2015/0164980 A1 6/2015 Chawla

FOREIGN PATENT DOCUMENTS

WO WO-00/018899 A2 4/2000
WO WO-2009/039957 A2 4/2009

OTHER PUBLICATIONS

Oguma et al, 2012. Tohoku J. Exp. Med, 227(3):217-223.*
Moledina et al, 2015. Seminars in Dialysis. 28(4): 377-383.*
Eknoyan, "Side effects of hemodialysis," N Engl J Med. 311(14):915-7 (1984).
International Search Report and Written Opinion for International Patent Application No. PCT/US15/59300, dated Feb. 19, 2016 (9 pages).
Mogielnicki et al., "Angiotensin II enhances thrombosis development in renovascular hypertensive rats," Thromb Haemost. 93(6):1069-76 (2005) (Abstract only) (2 pages).
Rocco et al., "Prevalence of missed treatments and early sign-offs in hemodialysis patients," J Am Soc Nephrol. 4(5):1178-83 (1993).
Sidhom et al., "Low-dose prazosin in patients with muscle cramps during hemodialysis," Clin Pharmacol Ther. 56(4):445-51 (1994).
Bowsher et al., "Reduction in slow intercompartmental clearance of urea during dialysis," J Lab Clin Med. 105(4):489-97 (1985).
Chawla et al., "Intravenous angiotensin II for the treatment of high-output shock (ATHOS trial): a pilot study," Crit Care. 18(5):534 (2014) (9 pages).
Kaplan et al., "Response to head-up tilt in cramping and noncramping hemodialysis patients," Int J Clin Pharmacol Ther Toxicol. 30(5):173-80 (1992).
Piergies et al., "Activation of renin-angiotensin system does not cause skeletal muscle cramps during hemodialysis," Int J Clin Pharmacol Ther Toxicol. 28(10):405-9 (1990).
Khanna et al., "Angiotensin II for the Treatment of Vasodilatory Shock," New Engl J Med. EPub:1-12 (2017).

* cited by examiner

*Primary Examiner* — Zachary Howard
(74) *Attorney, Agent, or Firm* — Clark & Elbing LLP

(57) ABSTRACT

Disclosed herein is a therapeutic intervention to prevent, reduce, or treat hemodialysis-associated skeletal muscle cramps by administering AII receptor agonists or other pharmacologic agents that augment homeostatic responses to hemodialysis while preventing derecruitment of skeletal muscle capillaries.

2 Claims, 1 Drawing Sheet

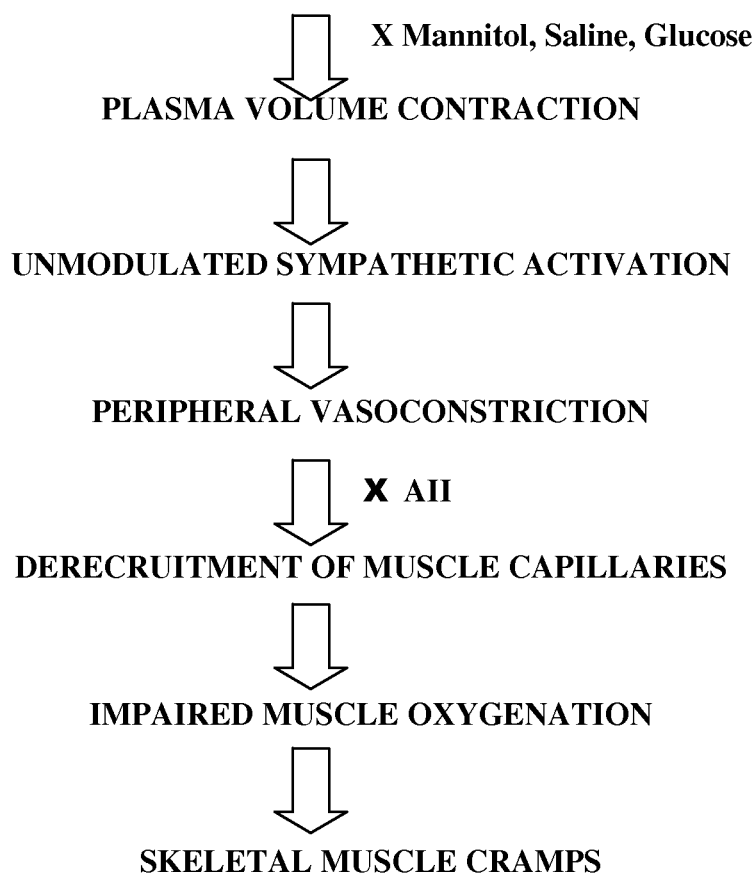

SEQUENCE LISTING

```
<160> NUMBER OF SEQ ID NOS: 4

<210> SEQ ID NO 1
<211> LENGTH: 10
<212> TYPE: PRT
<213> ORGANISM: Homo sapiens

<400> SEQUENCE: 1

Asp Arg Val Tyr Ile His Pro Phe His Leu
1               5                   10

<210> SEQ ID NO 2
<211> LENGTH: 8
<212> TYPE: PRT
<213> ORGANISM: Homo sapiens
```

```
<400> SEQUENCE: 2

Asp Arg Val Tyr Ile His Pro Phe
1               5

<210> SEQ ID NO 3
<211> LENGTH: 7
<212> TYPE: PRT
<213> ORGANISM: Homo sapiens

<400> SEQUENCE: 3

Arg Val Tyr Ile His Pro Phe
1               5

<210> SEQ ID NO 4
<211> LENGTH: 6
<212> TYPE: PRT
<213> ORGANISM: Homo sapiens

<400> SEQUENCE: 4

Val Tyr Ile His Pro Phe
1               5
```

USE OF ANGIOTENSIN II (AII) RECEPTOR AGONISTS TO PREVENT OR REDUCE HEMODIALYSIS-ASSOCIATED SKELETAL MUSCLE CRAMPS

CROSS REFERENCED TO RELATED APPLICATION

This application claims the benefit of priority under 35 USC 119(e) to U.S. provisional application No. 62/135,981, filed Mar. 20, 2015, which is herein incorporated by reference.

FIELD OF THE INVENTION

In general, the invention relates to a novel method of preventing or reducing hemodialysis-associated skeletal muscle cramps by using AII receptor agonists or other pharmacologic agents during hemodialysis to maintain capillary patency by modulating sympathetic nervous system response that the volume stress imposed by hemodialysis.

BACKGROUND OF THE INVENTION

Eknoyan (N Engl J Med 1984;311:915-7) estimated that intradialytic skeletal muscle cramps affect over one-third of hemodialysis patients. These cramps can be extremely painful and are a major cause of patient non-adherence to prescribed hemodialysis therapy. Over a 12-month period, Rocco and Burkart (J Am Soc Nephrol 1993;4:1178-83) reviewed 31,212 hemodialysis sessions in an average of 231 patients and found that missed treatments averaged 1.2±0.2% per month and early termination of dialysis sessions averaged 6.8±0.9% per month. Intradialytic skeletal muscle cramps were the most common single cause of this latter problem, being cited as the reason in 17.9% of the early terminations.

There have been few studies of the pathophysiology of intradialytic skeletal muscle cramps. However, there is general agreement that plasma volume contraction is the initiating event (FIG. 1). This is supported by the fact that typical treatment regimens for these cramps include administration of normal or hypertonic saline, hypertonic glucose and/or hypertonic mannitol, in addition to reducing ultrafiltration rate. However, postdialysis retention of sodium and mannitol may lead to increased thirst, interdialytic weight gain, and elevated blood pressure. Therefore, a number of prophylactic therapies have been advocated, including quinine, nifedipine, creatine, and shakuyaku-kanzo-to. Despite reports of the therapeutic success of these agents, no convincing pharmacologic rationale has been provided to support their claimed efficacy, and quinine, in particular, has an inadequate benefit-to-risk ratio to warrant its therapeutic use except in some patients with malaria. Consequently, there are no currently approved drugs or methods of treatment for cramping during dialysis. Therefore, there is a need for treatments that can prevent or ameliorate skeletal muscle cramps that occur during dialysis.

SUMMARY OF INVENTION

The present invention features the novel use of angiotensin II (AII) receptor agonists to prevent or reduce intradialytic skeletal muscle cramps. According to the invention, AII agonists are administered to dialysis patients before, during, or after treatment.

Therapeutic Agents

A preferred agent for therapeutic use in the invention is angiotensin II itself, which is a peptide with the sequence (from N-terminus to C-terminus) of Asp-Arg-Val-Tyr-Ile-His-Pro-Phe (SEQ ID NO:2). Other. therapeutic agents that may be used include angiotensin II agonistic peptides such as angiotensin III and angiotensin IV. The sequences of these peptides are as follows.

Angiotensin III: Arg-Val-Tyr-Ile-His-Pro-Phe (SEQ ID NO:3)

Angiotensin IV: Val-Tyr-Ile-His-Pro-Phe (SEQ ID NO:4)

In another embodiment, the invention features pro-drug forms of angiotensin II agonists for the treatment of dialysis cramping. One example of an angiotensin II pro-drug is the peptide angiotensin I, which has the sequence Asp-Arg-Val-Tyr-Ile-His-Pro-Phe-His-Leu (SEQ ID NO:1). Another example of an angiotensin II prodrug is the protein angiotensinogen, which is a 452-amino acid protein, which is cleaved by a protease, renin, to produce angiotensin I.

In another embodiment, the invention further features molecules that may stimulate the formation of angiotensin II from endogenous precursors for the treatment, reduction, or prevention of dialysis cramping. For example, administration of renin may be used to for this purpose. Alternatively, the enzyme angiotensin-converting enzyme (ACE) may be used to prevent, reduce, or treat dialysis cramping.

The invention also features the use of non-peptide agonists of angiotensin II for the prevention, reduction, or treatment of dialysis cramping. Methods for designing and synthesizing non-peptidic chemical structures are well known in the art of medicinal chemistry.

Therapeutic Agent Administration

In general, an angiotensin II agonist may be administered to a patient orally, by subcutaneous, intramuscular, intravenous or other modes of injection, or in any other manner. In one embodiment of the invention, an angiotensin II agonist is administered to a patient before or during dialysis, using the same intravenous line that is established for the dialysis itself. In a preferred version of this embodiment, the angiotensin II agonist is added into the distal injection port of the hemodialysis machine in the line that returns blood from the dialysis cartridge to the patient.

The dose of an angiotensin II agonist that is used depends on the particular agonist that is employed. For example, when angiotensin II itself is used, a preferred dose is between 0.1 and 250 ng/kg of body weight per minute of administration. More preferably a dose between 0.5 and 50 ng/kg·min is used. Even more preferably a dose between 2.5 and 10 ng/kg·min is used. According to one embodiment of the invention, a dose of 5 ng/kg·min is used, but this may have to be increased or decreased to meet the requirements of individual patients. According to another embodiment of the invention, an initial dose of 1 ng/kg·min is used and is increased over time (e.g., by 1 ng/kg·min every 15 minutes) until a final dose of 5 ng/kg·min is reached. The dose may be decreased (e.g., if systolic blood pressure rises more than 10 mmHg) or increased (e.g., if systolic pressure falls more than 10 mmHg) during administration of the angiotensin II agonist.

A preferred embodiment of the invention is to treat a patient at risk for dialysis cramping with an angiotensin II agonist that has a relatively short serum half-life, preferably a serum half-life of less than two hours, and more preferably less than one hour. For example, angiotensin II itself has a terminal serum half-life of less than 30 minutes. Angiotensin III and angiotensin IV also have serum half-lives of less than one hour. Without wishing to be bound by theory, the rationale for this aspect of the invention is that it minimizes possible undesirable side effects of angiotensin II agonists that are particularly manifested in conditions of long-term exposure. This is accomplished by reasonably rapid disappearance of the administered angiotensin II agonist subsequent to the termination of dialysis.

DESCRIPTION OF THE DRAWING

FIG. 1 is a diagram showing the proposed pathogenesis of hemodialysis-associated skeletal muscle cramps and mechanism by which angiotensin II agonists can prevent them. Mannitol, saline, and hypertonic glucose are believed to work by reducing plasma volume contraction but undesirably increase solute load. No integrated pharmacologic rationale has been proposed for other interventions that have been attempted.

DETAILED DESCRIPTION OF THE INVENTION

Muscle cramping during hemodialysis has been observed for several decades. These cramps are often severe, extremely unpleasant, and a leading cause of patient non-compliance to prescribed hemodialysis. In spite of this, there are no approved drug-based treatments for cramping during dialysis.

The present invention features the insight that dialysis cramps can be prevented, reduced, or treated by angiotensin II agonists, such as angiotensin II itself. Without wishing to be bound by theory, it is believed that, because angiotensin II (AII) acts on postcapillary as well as precapillary resistances, it is able to increase peripheral vascular resistance while maintaining capillary patency. This provides an advantage over agents that activate the sympathetic nervous system, releasing norepinephrine, because such activation only effects precapillary resistances and results in capillary derecruitment. Concomitant activation of both the sympathetic nervous system and renin-angiotensin system can prevent capillary derecruitment during hemodialysis. Conversely, a further insight of the invention is that patients who cramp frequently during hemodialysis have a sympathetic nervous system response to this volume stress that is not modulated by concomitant renin-angiotensin response and this results in derecruitment of skeletal muscle capillaries and cramping. Without wishing to be bound by theory, it is likely that administration of exogenous AII agonists can augment blood pressure homeostasis during hemodialysis and that its dual action on precapillary as well as postcapillary resistances can modulate sympathetic nervous system responses, thereby preventing intradialytic skeletal muscle cramps.

Further, the action of AII agonists which distinguishes them from the adrenergic agents employed to treat hemodialysis-associated hypotension also makes them a preferred treatment for this hemodialysis complication and for patients with septic and other forms of shock.

Angiotensin II (AII) is an octapeptide having a molecular weight of 1046.2 Daltons and the following structure:

H-Asp-Arg-Val-Tyr-Ile-His-Pro-Phe-OH (SEQ ID NO:2)

AII is the classical effector of the renin-angiotensin cascade and is formed endogenously from angiotensinogen by two successive hydrolytic reactions. Several AII polypeptide metabolites of AII also act on angiotensin receptors, and it is likely that small molecule agonists can also be developed and employed. AII is available commercially for clinical research as a sterile dry powder supplied in glass vials. It is intended to be administered intravenously after reconstitution in physiological saline.

Although AII has been administered to human subjects both by injection and infusion, it is the prior experience with infusions that is most relevant to the current use of this agent. AII infusions generally have been used to probe physiological responses in normal subjects and in patients, but in a few instances have been administered as therapy to treat patients with septic shock that has become refractory to catecholamines, during cesarean section to maintain blood pressure during spinal anesthesia, and to deliver intra-arterial chemotherapy more selectively.

Proposed Clinical Use of Angiotensin II (AII) and/or Other AII Receptor Agonists Depending on the specific application, angiotensin II will generally be administered as infusions to patients beginning at the start of hemodialysis and continuing through this procedure. It is convenient to administer these infusions through the injection port in the hemodialysis circuit that returns blood to the patient after passing through the dialyzer. An effective dose is 5 ng/kg·min but this dose may have to be adjusted in individual patients. During administration, the dose may be increased if cramping occurs to maintain skeletal muscle capillary patency by preventing capillary derecruitment while augmenting blood pressure homeostatic mechanisms, or decreased to prevent excessive increments in blood pressure.

Angiotensin II is superior to catecholamines to maintain blood pressure in patients who would otherwise suffer from hemodialysis-associated hypotension. Other angiotensin II agonists such as metabolites or orally active small molecules that are angiotensin receptor agonists may be used.

Because of the effect of angiotensin II agonists on the circulatory system, it is often useful to consider several factors when prescribing or administering an angiotensin II agonist. Such factors include:
  Concomitant therapy with angiotensin receptor blocking drugs
  Any known (history or presence of any) aortic or peripheral arterial aneurysm
  Congestive heart failure, myocardial infarction, or cerebrovascular infarct or hemorrhage within the previous 3 months
  Symptomatic cardiac arrhythmias or angina pectoris
  Termination of a treadmill test for reasons other than claudication (eg, arthritis, lung disease, exercise-limiting cardiac disease, or skin or foot lesions that limit walking)

Uncontrolled hypertension; supine arterial systolic BP>140 mmHg or diastolic BP>100 mmHg at screening Current treatment with anticoagulants (e.g. heparin or heparin-like compounds, warfarin)

Known bleeding disorder

Platelet count<50,000, bilirubin or AST or ALT>2× the upper limit of normal

Pregnancy, lactation or plans to become pregnant during the course of treatment

Morbid obesity, such as a body mass index greater than 40

Manufacture, Formulation, and Administration of Therapeutic Agents

The methods of manufacturing angiotensin II agonists vary depending on the agonist to be used. For example, the methods for manufacturing peptides such as angiotensin II itself are well known in the art of synthetic organic chemistry and biotechnology.

In one embodiment, glass vials containing 50 µg angiotensin II (AII) packaged under inert gas (for example, supplied by Bachem) are used, along with pumps for administering AII infusions. AII is reconstituted in 5% D/W and added to a 250 mL glass bottle of 5% D/W to give a final concentration of Dose x Patient Weight (in kg) per mL, where Dose initially is 1 ng/kg or 2 ng/kg, but may subsequently be between 1 and 5 ng/kg or 1 and 10 ng/kg (for example, 3, 5, or 10 ng/kg), as specified by the protocol. The infusion pump delivers infusions at a rate of 0.5 mL/min or 1 mL/min but may be altered to deliver less than 0.5 mL/min or as much as 2 mL/min, as needed. The infusion rate may be lowered to 0.5 mL/min should systolic pressure rise more than 15 mm Hg. It may be preferred to use infusion pumps that are accurate at lower infusion rates, in which case the dissolved Dose would be correspondingly increased.

EXAMPLE

The following example is provided for the purpose of illustrating the invention and should not be construed as limiting.

Example 1

Treatment of a Patient with an Angiotensin II Agonist During Hemodialysis

A typical hemodialysis patient at risk for dialysis-associated cramping is treated as follows. The patient is administered a 1 ng/kg·min angiotensin II infusion through the venous port of their hemodialysis line. Blood pressure is monitored before hemodialysis and during the infusion at 15-minute intervals. The infusion rate is increased to 2 ng/kg·min if systolic blood pressure has not increased by more than 10 mm Hg above pre-dialysis levels. The infusion rate is increased in increments of 1 ng/kg·min every 15 minutes to a maximum infusion rate of 5 ng/kg·min if the increase in systolic pressure remains less than 10 mm Hg above pre-dialysis levels and the infusion rate is well tolerated by the patient. At any point the infusion rate is decreased by an increment of 1 ng/kg·min if systolic pressure rises more than 10 mm Hg or is increased by an increment of 1 ng/kg·min if systolic pressure falls more than 10 mm Hg below pre-dialysis levels. The infusion is tapered in decrements of 1 ng/kg·min or discontinued if an increase of the systolic pressure is greater than 15 mm Hg or the patient reports headaches or other symptoms attributable to excess angiotensin II. The infusion rate is again increased by increments of 1 ng/kg·min to a maximum infusion rate of 5 ng/kg·min every 15 minutes if systolic pressure falls below its pre-dialysis levels. Tolerability of the final selected infusion rate is confirmed during the next hemodialysis session. Blood is optionally obtained just before the conclusion of such a dialysis session for measurement of AII plasma concentrations and estimation of AII elimination clearance.

Other Embodiments

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents, and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

Other embodiments are in the claims.

What is claimed is:

1. A method of preventing, reducing, or treating cramping during hemodialysis, said method comprising administering to a subject an effective amount of angiotensin II.

2. The method of claim 1, wherein the effective amount of angiotensin II is between 0.1 and 250 ng/kg of body weight of the subject.

* * * * *